United States Patent
Kalalakaran et al.

(10) Patent No.: US 10,679,726 B2
(45) Date of Patent: Jun. 9, 2020

(54) DIAGNOSTIC GENETIC ANALYSIS USING VARIANT-DISEASE ASSOCIATION WITH PATIENT-SPECIFIC RELEVANCE ASSESSMENT

(71) Applicant: KONINKLIJKE PHILIPS N. V., Eindhoven (NL)

(72) Inventors: Sitharthan Kalalakaran, Pelham, NY (US); Vinay Varadan, New York, NY (US); Nilanjana Banerjee, Armonk, NY (US); Angel Janevski, New York, NY (US); Nevenka Dimitrova, Pelham Manor, NY (US)

(73) Assignee: Koninklijke Philips N.V., Eindhoven (NL)

( * ) Notice: Subject to any disclaimer, the term of this patent is extended or adjusted under 35 U.S.C. 154(b) by 517 days.

(21) Appl. No.: 14/441,020

(22) PCT Filed: Nov. 15, 2013

(86) PCT No.: PCT/IB2013/060150
§ 371 (c)(1),
(2) Date: May 6, 2015

(87) PCT Pub. No.: WO2014/080323
PCT Pub. Date: May 30, 2014

(65) Prior Publication Data
US 2015/0294063 A1    Oct. 15, 2015

Related U.S. Application Data

(60) Provisional application No. 61/729,678, filed on Nov. 26, 2012.

(51) Int. Cl.
*G16B 20/00* (2019.01)
*G16B 40/00* (2019.01)
(Continued)

(52) U.S. Cl.
CPC ............ *G16B 20/00* (2019.02); *G16B 30/00* (2019.02); *G16B 40/00* (2019.02); *G16H 50/20* (2018.01)

(58) Field of Classification Search
None
See application file for complete search history.

(56) References Cited

U.S. PATENT DOCUMENTS 7,206,699 B2  4/2007  Larder et al.
7,494,768 B1  2/2009  Hertogs et al.
(Continued)

FOREIGN PATENT DOCUMENTS

WO    2011076783 A2    6/2011

OTHER PUBLICATIONS

M Kanehisa and S Goto. KEGG: Kyoto Encyclopedia of Genes and Genomes. Nucleic Acids Research 2000, vol. 28, No. 1, p. 27-30 (Year: 2000).*

(Continued)

*Primary Examiner* — Olivia M. Wise

(57) ABSTRACT

Relevance of a study genetic variant observed in diagnostic subject genetic data that is associated by a clinical study with a phenotype characteristic is assessed as follows. A set of polymorphisms functionally related to the study genetic variant are identified. A foreground distribution is computed of variants observed in the diagnostic subject genetic data for the set of polymorphisms. A background distribution is computed of variants observed in genetic data of subjects of the clinical study for the set of polymorphisms. A comparison metric is computed comparing the foreground distribution and the background distribution. Relevance of the study variant to the diagnostic subject is quantified based on the (Continued)

Figure 1:
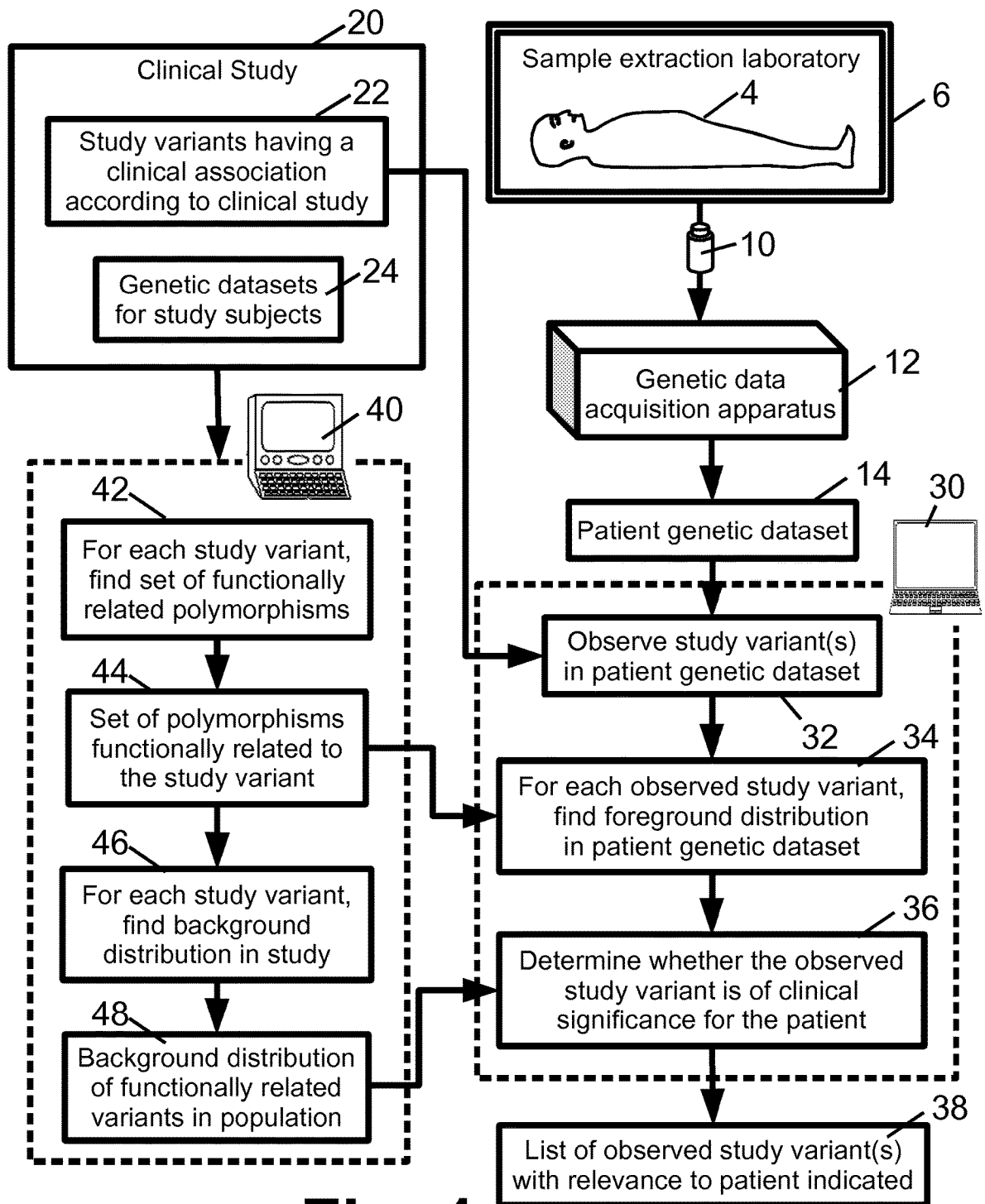

comparison metric, with higher similarity of the foreground and background distributions corresponding to higher relevance.

19 Claims, 5 Drawing Sheets

(51) Int. Cl.
  *G16H 50/20* (2018.01)
  *G16B 30/00* (2019.01)

(56) References Cited

U.S. PATENT DOCUMENTS

| | | |
|---|---|---|
| 2003/0022223 A1 | 1/2003 | Rone |
| 2004/0219567 A1 | 11/2004 | Califano et al. |
| 2008/0286796 A1 | 11/2008 | Grupe et al. |
| 2008/0299554 A1 | 12/2008 | Huang et al. |
| 2009/0029375 A1 | 1/2009 | Jupe et al. |
| 2013/0332081 A1* | 12/2013 | Reese ............ G06F 19/18 702/19 |

OTHER PUBLICATIONS

Berry et al. Matrices, Vector Spaces, and Information Retrieval. SIAM Review, vol. 41, No. 2, pp. 335-362 (Year: 1999).*

Carbonell, J. et al, "A map of human microRNA variation uncovers unexpectedly high levels of variability", Genome Med. Biomed Central Ltd., London, UK, vol. 4, No. 8, Aug. 24, 2012, p. 62.

Jeanpierre, C. et al, "Software and database for the analysis of mutations in the human WT1 gene", Nucleic Acids Research, Oxford Univ. Press,, London, vol. 26, No. 1, Jan. 1, 1998, pp. 271-274.

* cited by examiner

US 10,679,726 B2

DIAGNOSTIC GENETIC ANALYSIS USING VARIANT-DISEASE ASSOCIATION WITH PATIENT-SPECIFIC RELEVANCE ASSESSMENT

CROSS-REFERENCE TO PRIOR APPLICATIONS

This application is the U.S. National Phase application under 35 U.S.C. § 371 of International Application No. PCT/IB2013/060150, filed on Nov. 15, 2013, which claims the benefit of U.S. Provisional Application No. 61/729,678, filed on Nov. 26, 2012. These applications are hereby incorporated by reference herein.

The following relates to the genetic analysis arts, medical arts, and to applications of same such as the medical arts including oncology arts, veterinary arts, and so forth.

A genome-wide association (GWA) study examines variants in the genome of different individuals to identify relationships between the variants found in different individuals and their phenotype such as disease susceptibility. Different variants are then associated with different traits, such as diseases. Such a clinical study identifies variants that can then be detected in patients and thus can serve as indicators for the associated disease (or other phenotype characteristic).

In humans, GWA studies have led to discovery of associations of particular genes with diseases such as the eye disease known as age-related macular degeneration and diabetes. Typically in these studies, hundreds to thousands of individuals are tested for hundreds of thousands of variants across their genome. The variants are usually of single-nucleotide polymorphisms, or SNPs. Over 1,200 human GWA studies have examined over 200 diseases and traits, and found almost 4,000 SNP associations.

The following contemplates improved apparatuses and methods that overcome the aforementioned limitations and others.

According to one aspect, a non-transitory storage medium stores instructions executable by an electronic data processing device to perform a method including: identifying a study genetic variant in diagnostic subject genetic data that is associated by a clinical study with a phenotype characteristic; identifying a set of polymorphisms functionally related to the study genetic variant; computing a foreground distribution of variants observed in the diagnostic subject genetic data for the set of polymorphisms; computing a background distribution of variants observed in genetic data of subjects of the clinical study for the set of polymorphisms; computing a comparison metric comparing the foreground distribution and the background distribution; and quantifying relevance of the study variant to the diagnostic subject based on the comparison metric.

According to another aspect, an apparatus comprises: a non-transitory storage medium as set forth in the immediately preceding paragraph; and an electronic data processing device configured to execute the instructions stored on the non-transitory storage medium.

According to another aspect, a method comprises: identifying a set of polymorphisms functionally related to a study genetic variant observed in diagnostic subject genetic data that is associated by a clinical study with a phenotype characteristic; computing a foreground distribution of variants observed in the diagnostic subject genetic data for the set of polymorphisms; computing a background distribution of variants observed in genetic data of subjects of the clinical study for the set of polymorphisms; and computing a comparison metric comparing the foreground distribution and the background distribution. The identifying a set of polymorphisms, the computing a foreground distribution, the computing a background distribution, and the computing a comparison metric are suitably performed by an electronic data processing device.

One advantage resides in providing patient-specific relevance assessment for genetic variants generally known to correlate with disease or another phenotype characteristic.

Another advantage resides in more accurate clinical testing using genetic markers. Numerous additional advantages and benefits will become apparent to those of ordinary skill in the art upon reading the following detailed description.

The invention may take form in various components and arrangements of components, and in various process operations and arrangements of process operations. The drawings are only for the purpose of illustrating preferred embodiments and are not to be construed as limiting the invention.

FIG. 1 diagrammatically shows a system for analyzing a patient genetic dataset to detect disease or another phenotype characteristic in the patient.

FIGS. 2-6 diagrammatically show detail drawings of selected components of the system of FIG. 1.

Genetic assessment typically includes acquiring patient genetic data and comparing it with genetic variants having disease associations (or other phenotype associations) as indicated by clinical studies. By way of illustrative example, the acquired patient genetic data may include a whole genome sequence (WGS) (typically considered as including at least 90% of the nuclear DNA content, and more typically 95% or more of the nuclear DNA content, and optionally also including RNA or other genetic sequencing data), genetic sequencing data comprising less than a WGS, genetic data acquired using a microarray, for example having hundreds of thousands of single nucleotide polymorphism (SNP) measurements (possibly including genetic data in the form of gene expression, i.e. proteomic, information), or so forth. For a large patient genetic dataset such as that produced by high-throughput genetic sequencing or microarray processing, thousands of genetic variants may be observed in the patient genetic data. Typically, tens to hundreds of these variants have been previously determined to be disease associated in some GWA study.

However, it is recognized herein that the risk associated with a genetic variant observed in a particular individual is not readily quantifiable for that individual on the basis of the clinical study results alone. One reason for this is that the association of the variant with a disease (or other phenotype characteristic) that was identified by a GWA study was identified in the context of a study population in which the clinical study was performed. For example if a GWA study was done primarily in a population of Central European descent, then the SNP association could be relevant only for patients of central European descent. Other populations such as persons of African or Asian descent could have compensatory variation in other genes in the same pathway that the disease associated SNP belongs to, thereby decreasing the significance of the disease association. Similarly, a GWA study may be limited to subjects of a single gender, or within a certain age bracket, or so forth. Whether these constraints on the study population actually affect the relevance of the variant-disease associations to a particular patient is not readily ascertained. For example, even though a given clinical study may have been performed on a population of central European descent, the resulting variant associations may nonetheless be relevant to persons of other ethnicities or they may not be relevant at all to such populations, or the relevance may be less for persons of other ethnicities.

Typically, a study publication includes demographic information about the population pool in which the study was performed. Based on this, a patient's physician can determine whether the clinical study results are applicable to the patient, and hence decide whether to order the test for the patient. However, there is generally no principled basis for the physician to make this decision. Seemingly minor demographic differences may in actually make the test inapplicable to the patient, whereas seemingly significant demographic differences may actually have little or no result on applicability to the patient. Moreover, differences between the patient and the study population that actually affect applicability of the test to the patient may not be recorded in the study publication.

Thus, when the patient appears to deviate from the study population pool, the physician is left with a difficult choice: apply the study results to the patient at the risk of obtaining a false result; or do not apply the study results to the patient at the risk of not obtaining probative medical information.

Solutions for these difficulties are presented herein. In these approaches, the expectation is that if the patient has a similar distribution of variants functionally related to the study variant whose relevance is being assessed as in the population used in the clinical study, then the study variant-disease association is likely to be significant in the patient and thus provides relevant clinical information for the patient.

Some comments on terminology used herein follow.

The term "diagnostic subject" is used herein to denote a patient, veterinary subject, forensic subject (e.g., a cadaver undergoing an autopsy), archaeological subject (e.g., a mummy or human remains), or so forth, from whom (or from which) diagnostic subject genetic data are obtained and compared with results of a clinical study for the purpose of identifying a disease or other phenotype characteristic in the diagnostic subject. The identification is done by observing a genetic variant in the diagnostic subject which the clinical study associates with a disease or other phenotype characteristic, and then assessing the actual relevance of that association to the diagnostic subject using approaches disclosed herein. In the illustrative embodiments the diagnostic subject is a patient and is referred to as such; however, the illustrative embodiments are readily applied to diagnostic subjects of other types (e.g., veterinary subjects, forensic subjects, et cetera). Subjects of the clinical study are typically of the same "type" as the diagnostic subject. Thus, a clinical study applied to a patient, human cadaver, or so forth, employs a human population; whereas a clinical study applied to a canine veterinary subject employs a canine subject population. In the case of an archaeological diagnostic subject, the population pool of the applied clinical study may comprise a modern living population, or may comprise a population of (other) archaeological remains.

As used herein, the term "polymorphism" is used to indicate a subsequence (its "location") having two or more different possible "variants". For example, a single nucleotide polymorphism (SNP) is designated by chromosome x location y, while a variant may be specified as nucleotide "A" (adenine) at chromosome x location y. A polymorphism is a genetic sub-sequence having two or more variants observed in the population. Typically, WGA studies identify single nucleotide polymorphisms (SNPs) in which the genetic sub-sequence is a single nucleotide location in the genome that has two or more different possible nucleotides (variants) occurring in the population. For example, a given SNP may normally have the nucleotide "A" (adenine) but in some individuals may have the nucleotide "G" (guanine), or less commonly the nucleotide "C" (cytosine). This illustrative SNP has three variants ("A", "G", and "C") occurring in the population. (Note, the terms "nucleotide" and "base" are used interchangeably herein).

Although SNPs are the polymorphisms most commonly characterized in clinical studies, a polymorphism can have other configurations. Other (non-exhaustive) examples of polymorphisms include: an insertion (the genetic subsequence may have an extra nucleotide inserted), a deletion (the genetic subsequence may have an omitted nucleotide), copy number polymorphism (the genetic subsequence may be duplicated one or more times), structural polymorphism (the genetic subsequence has a two or more possible secondary structure configurations), methylation polymorphism (the genetic subsequence may include a methylated nucleotide), or so forth. Polymorphisms as used herein also include sequence polymorphisms, i.e. locations where more than one sequence can occur. For example, a variant in the form of a dinucleotide can exist at a position, or a gene can be present in one or more copies in the genome. As used herein, "genetic polymorphism" or simply "polymorphism" refers to the subsequence (in effect, the "location" in the genome) while "genetic variant" or simply "variant" refers to a particular value of the polymorphism (e.g., the specific nucleotide for an SNP, or the specific sequence in the case of a sequence polymorphism). So, for example, an SNP may be specified by its location x in chromosome C, and may have possible variants "A", "C", or "G" in the foregoing example. The variant is therefore fully specified by its location and the value at that location (e.g., a variant may be specified as having the nucleotide "A" at location x in chromosome C).

With reference to FIG. 1, a system is described for diagnosing (i.e., identifying) a disease or other phenotype characteristic in a diagnostic subject 4 (namely a patient in these illustrative examples). The patient 4 undergoes a sample extraction procedure in a sample extraction laboratory 6 to extract an oral swab, biopsy sample, or other tissue sample 10 (diagrammatically indicated in FIG. 1 by a vial, but suitably may be carried by a slide or other suitable tissue sample container or support) that is processed by a genetic data acquisition apparatus 12 to generate a diagnostic subject genetic dataset 14 (namely a patient genetic dataset in the illustrative examples).

In some embodiments, the genetic data acquisition apparatus 12 is a genetic sequencing system including a sequencer that generates sequencing reads and suitable data processing hardware (e.g., a suitably programmed computer) to preprocess and align the reads (optionally with mapping to a reference sequence) to generate a whole genome sequence (WGS) or lesser portion of the genome. The data processing generating the patient genetic dataset 14 may further include annotation operations, for example labeling of known variants. The sequencer apparatus may be a next generation sequencing (NGS) apparatus or a more conventional sequencing apparatus such as a Sanger sequencing facility. The sequencer apparatus may in some embodiments be a commercial sequencing apparatus such as are available from Illumina, San Diego, Calif., USA; Knome, Cambridge, Mass., USA; Ion Torrent Inc., Guilford, Conn., USA; or other NGS system vendors; however, a noncommercial or custom-built sequencer is also contemplated.

Additionally or alternatively, the genetic data acquisition apparatus 12 may include microarray processing hardware by which the tissue sample 10 is processed to generate microarray data. In a conventional configuration, the microarray includes a large number of cells (e.g., 600,000 cells in some embodiments, although more or fewer cells are contemplated) with each cell including adherents, chemicals, or so forth to measure a particular genetic marker, such as the expression level of a particular protein. In this regard, it should be noted that "genetic data" as used herein is intended to broadly encompass proteomic data (e.g., gene expression levels), methylation data, or so forth, in addition to gene sequencing data. It is also contemplated for the patient genetic dataset 14 to include a combination of genetic data from different sources, e.g. sequencing data generated by a sequencing apparatus and protein expression levels from microarray analysis. It is still further to be understood that operation of the genetic data acquisition apparatus 12 may entail some manual operations, e.g. sample preparation and loading operations performed by suitably trained personnel.

To perform diagnostic analysis, the patient genetic dataset 14 is compared with results of a clinical study 20. These results include study genetic variants 22 which have been associated by the clinical study 20 with a disease or other phenotype characteristic. The results of the clinical study 20 also include the "raw data", i.e. the genetic datasets 24 acquired for the study subjects. Typically, the clinical study 20 is a published study that has been published in a peer-reviewed medical journal, and the genetic datasets 24 are available in a publically accessible data repository maintained by the journal or by a medical society or other entity associated with the journal. Alternatively, the clinical study 20 may be an unpublished study, for example a proprietary study performed by a medical services company to generate variant-disease association data for use in a commercial genetic testing service. In this case, the subject genetic datasets 24 are suitably stored on a private server or other data processing facility of the medical services company.

The diagnostic analysis is suitably performed by a computer 30 or other electronic data processing device that performs operations 32, 34, 36 diagrammatically indicated in FIG. 1. In the operation 32, the patient genetic dataset 14 is searched to determine whether any of the study genetic variants 22 identified by the clinical study 20 as having disease (or, more generally, phenotype characteristic) associations are observed in the patient genetic dataset 14. The variant identification operation 32 suitably refers to variant annotations or other annotations of the patient genetic dataset 14 if such annotations are available. Additionally or alternatively, sub-sequence pattern matching can be employed to identify genetic variants in sequencing data. For microarray data, each array cell is typically known to test for a particular genetic marker, and so correlation with the study variants 22 is straightforward. Quantification of the observation of a variant can take various forms. In the case of an SNP, the observation of a variant may be binary either the SNP location in the patient genetic dataset 14 has the variant nucleotide, or it does not. In the case of gene expression measured by a microarray, a threshold can be used to generate a binary observation (e.g., the gene expression level is higher than the threshold, or it is not). Alternatively, the observation can be a non-binary quantity, e.g. the actual protein expression level when it is high enough to be considered an observed variant.

The output of the observation operation 32 is conventionally taken as the output of the genetic test, that is, the observation of the study variant is taken as evidence that the patient has the associated disease (or phenotype characteristic). However, this makes the assumption that the variant-disease association determined by the clinical study 20 is valid for the particular patient 4, which may not be the case if the patient is of a different demographic group or is otherwise "significantly" different from the study population. In such cases, the variant-disease association may not be valid for the patient 4, or may be valid to a lesser extent than would be assumed based on the results of the clinical study 20.

Accordingly, in the diagnostic system of FIG. 1 the further operations 34, 36 are performed to assess relevance of the variant-disease association to the particular patient 4 undergoing diagnosis. The approach used is to (1) identify a "foreground" distribution of variants observed in the patient genetic dataset 14 for a set of polymorphisms that are functionally related to the observed study variant (operation 34) and (2) compare this foreground distribution with a "background" distribution of variants observed in the subject genetic datasets 24 for the same set of polymorphisms (operation 36). In this analysis, the closeness of the match is determined by taking each polymorphism in the set of functionally related polymorphisms in the patient (foreground) and calculating the probability of its occurrence in the "background" population. In this case the background population is the population in which the clinical relevance of the polymorphism was established. Given the allele frequencies of the polymorphism in the background set, one can assess the probability of each of the patient polymorphism in the background set and collectively establish the joint probability of finding an individual with the patient polymorphisms in the background set. This probability is converted to a closeness score using standard methods (e.g. through the use of a linear or similar monotonic function). The joint probability for the entire set of polymorphisms under study is calculated in a naive Bayesian approach assuming independence of the polymorphisms being considered or through a Bayesian network model that captures the haplotype relationship. In the operation 36, a close match between the foreground and background distributions is taken to indicate that the patient 4 is a close match with the subject pool of the clinical study 20, and so the disease association of the study variant determined by the study 20 is considered to be relevant to the patient 4. On the other hand, a substantial mismatch between the foreground and background distributions is taken to indicate that the patient 4 differs from the subject pool of the clinical study 20 in a significant way (since the differences relate to polymorphisms functionally related to the study variant), and so the disease association of the study variant determined by the study 20 is not considered to be relevant to the patient 4. More generally, the operation 36 typically employs a quantitative similarity (or distance) measure (generally encompassed by the term "comparison metric") comparing the foreground and background distributions, and this comparison metric provides a relevance quantification which is not necessarily binary (although a binary "relevant-or-irrelevant" decision can be made by thresholding the comparison metric). In an operation 38, the observed study variant or variants can then be listed along with an indication of the relevance of each observed genetic variant to the patient 4.

The operation 34 requires as input the set of polymorphisms that are functionally related to the observed study variant. The operation 36 requires as input the foreground distribution (from operation 34) and the background distribution. Both the set of functionally related polymorphisms and the background distribution can optionally be determined for each study variant prior to performing the diagnostic operations 32, 34, 36, 38 for the patient 4. Such "offline" determination of the set of functionally related polymorphisms and the background distribution for each study variant can improve computational efficiency, since this information is independent of the patient 4. Accordingly, in the diagnostic system of FIG. 1 a separate computer 40 or other electronic data processing device performs an operation 42 in which a set of polymorphisms 44 which are functionally related to the study variant is determined, and performs an operation 46 in which a background distribution 48 of variants observed in the subject genetic datasets for the set of polymorphisms 44 is determined. The set of functionally related polymorphisms 44 and the background distribution 48 of the variants is computed for each study variant, since in general each study variant may have a different set of functionally related polymorphisms. In general, the set of polymorphisms 44 may include any type of polymorphism, e.g. SNPs, sequence polymorphisms (e.g., gene copies, locations containing multi-nucleotide variants, et cetera). However, for computational efficiency it is contemplated in some embodiments to limit the set of polymorphisms 44 to SNPs.

As just discussed, performing the operations 42, 46 offline, that is, predetermining the set of functionally related polymorphisms 44 and the background distribution 48 for each study variant before commencement of the patient diagnosis operations 32, 34, 36, is computationally efficient when a large throughput of patients is expected, as in the illustrative case of a commercial medical services provider. However, it is also contemplated to perform the operations 42, 46 at the time of patient diagnosis. Similarly, while separate computers 30, 40 are shown performing the patient-diagnostic operations 32, 34, 36, and the non-patient-specific pre-computation operations 42, 46, it is also contemplated to employ the same computer for both sets of operations. (Said another way, in some embodiments the two illustrated computers 30, 40 may be a single computer that performs all operations 32, 34, 36, 42, 46.)

Figure 2:
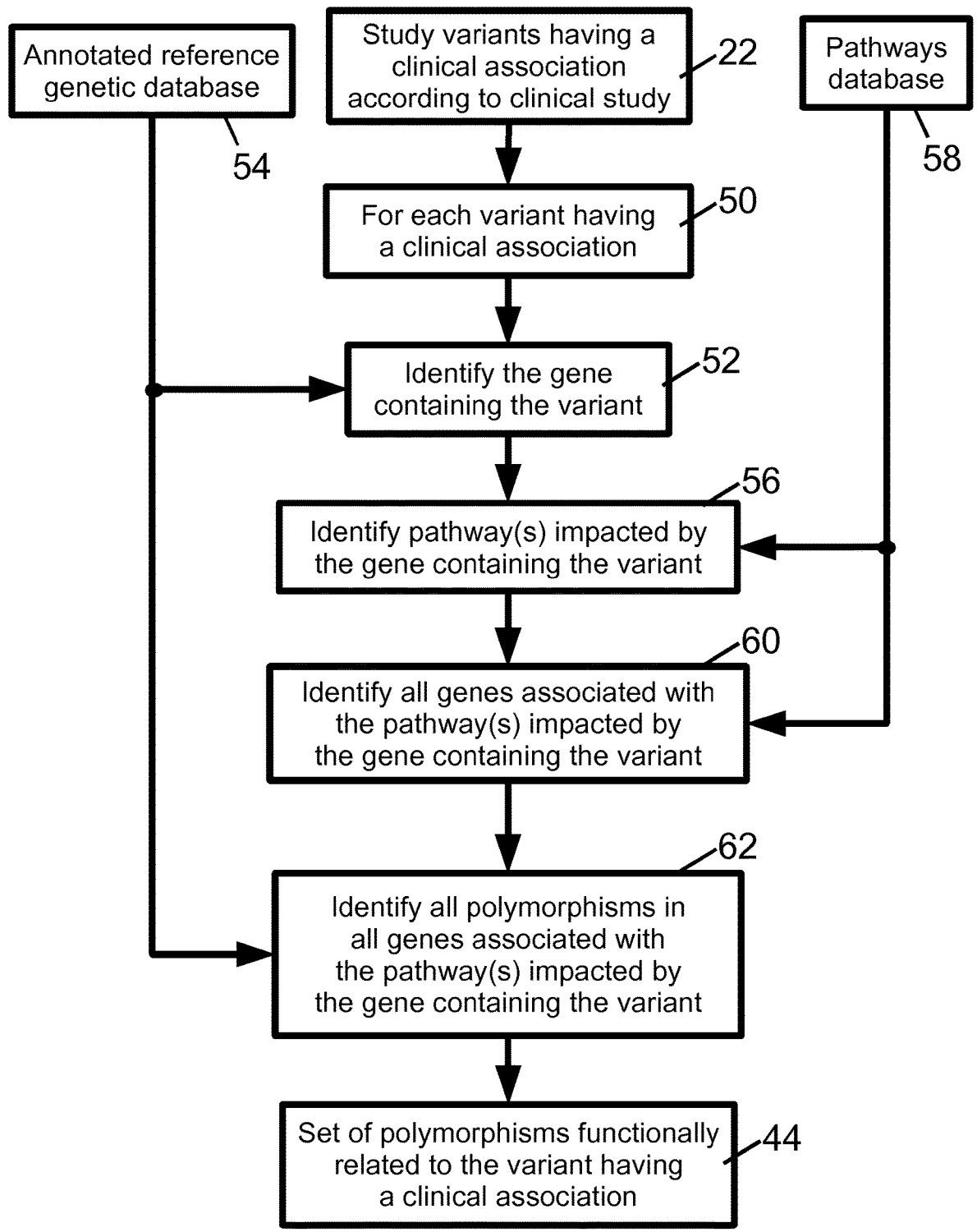
Figure 3:
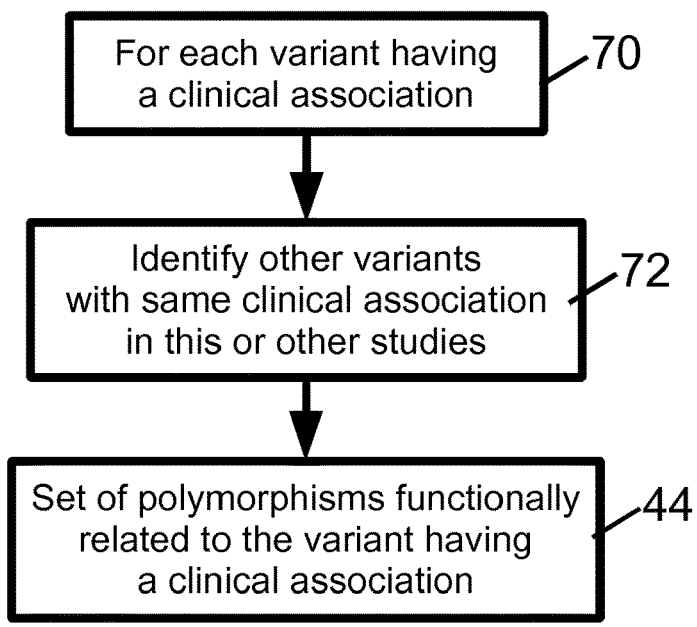
Figure 4:
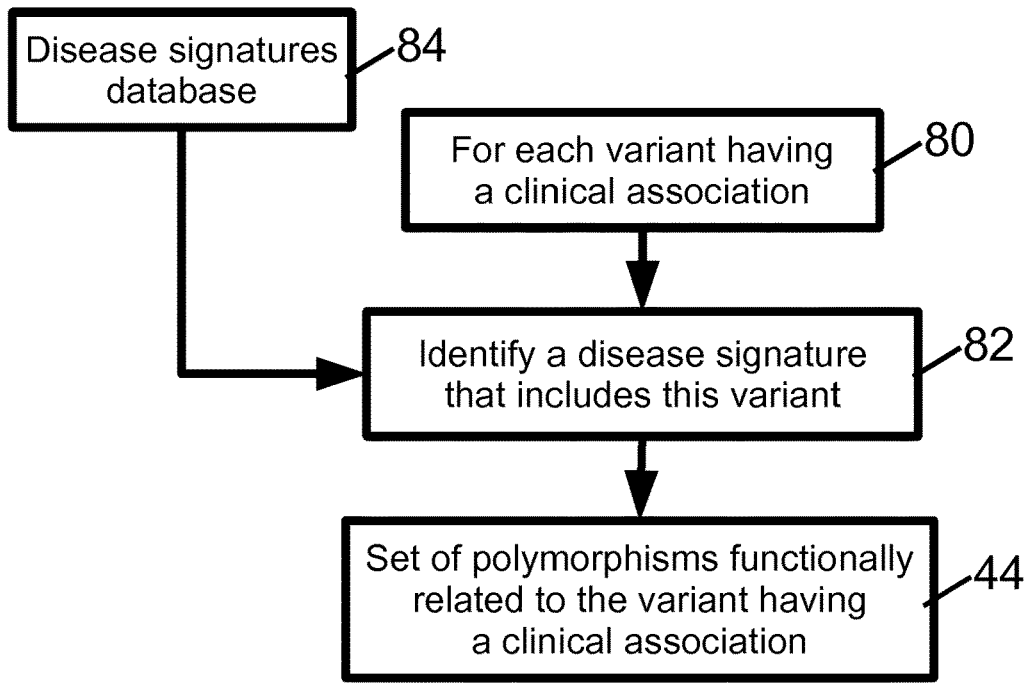

With reference to FIGS. 2-4, various approaches can be used to perform the operation 42 which identifies the set of functionally related polymorphisms 44.

With reference to FIG. 2, in one approach the operation 42 identifies a genetic pathway with which the study genetic variant is associated, and identifying polymorphisms associated with the identified genetic pathway. Toward this end, for each study variant having a clinical association 50, the gene containing that study variant is identified in an operation 52. The gene identification can be performed, for example, by referencing an annotated reference genetic database 54. In some embodiments, the genetic sequencing operations include annotating the patient genetic dataset 14 with gene identifications, in which case the operation 52 is suitably omitted (as it is subsumed into post-acquisition data processing operations performed by the acquisition apparatus 12 in these embodiments). In an operation 56, the genetic pathway (or pathways) impacted by the gene containing the study variant are identified. The operation 56 suitably accesses a pathways database 58 to make this identification. For example, the pathways database 58 may be the Kyoto Encyclopedia of Genes and Genomes (Kegg) pathway database. In an operation 60, all genes associated with the genetic pathway (or pathways) impacted by the gene containing the study variant are identified. The operation 60 can again access the pathways database 58 to make this identification. In an operation 62, all polymorphisms in genes associated with the genetic pathway (or pathways) impacted by the gene containing the study variant are identified, and these form (or are included in) the set of polymorphisms 44 deemed to be functionally related to the study variant. The operations 50, 52, 56, 60, 62 are repeated for each study variant of the set of study variants 22 identified by the clinical study 20.

With reference to FIG. 3, in another approach the operation 42, for each study variant 70, performs an identification operation 72 which identifies other genetic variants having the same clinical association as that of the study variant. These other variants having the same clinical association may be identified in the same study 20, or optionally may be identified by other clinical studies. For example, if the study genetic variant is associated with ocular macular degeneracy by the study 20, then the operation 72 identifies other genetic variants that have been identified as being associated with ocular macular degeneracy. The polymorphisms corresponding to these variants identified by operation 72 then form (or are included in) the set of polymorphisms 44 deemed to be functionally related to the study variant. The operations 70, 72 are repeated for each study variant of the set of study variants 22 identified by the clinical study 20.

With reference to FIG. 4, in another approach the operation 42, for each study variant 80, performs an identification operation 82 which identifies a disease signature including the study variant. The identification operation 82 suitably references a disease signatures database 84 or other literature defining disease signatures. The polymorphisms corresponding to other variants of the disease signature containing the study variant then form (or are included in) the set of polymorphisms 44 deemed to be functionally related to the study variant. The operations 80, 82 are repeated for each study variant of the set of study variants 22 identified by the clinical study 20.

The illustrative examples suitable approaches for performing the operation 42 described with reference to FIGS. 2-4 are merely examples, and other approaches can be used to identify the set of polymorphisms 44 deemed to be functionally related to the study variant. Moreover, the approaches of FIGS. 2-4 can be variously combined. For example, the operation 42 can employ the pathway analysis approach of FIG. 2 to identify some functionally related polymorphisms, and can reference a known disease signature containing the study variant as per FIG. 4 to identify additional functionally related polymorphisms, and the final set of functionally related polymorphisms 44 is the combination of the outputs of the two processes of respective FIGS. 2 and 4.

Figure 5:
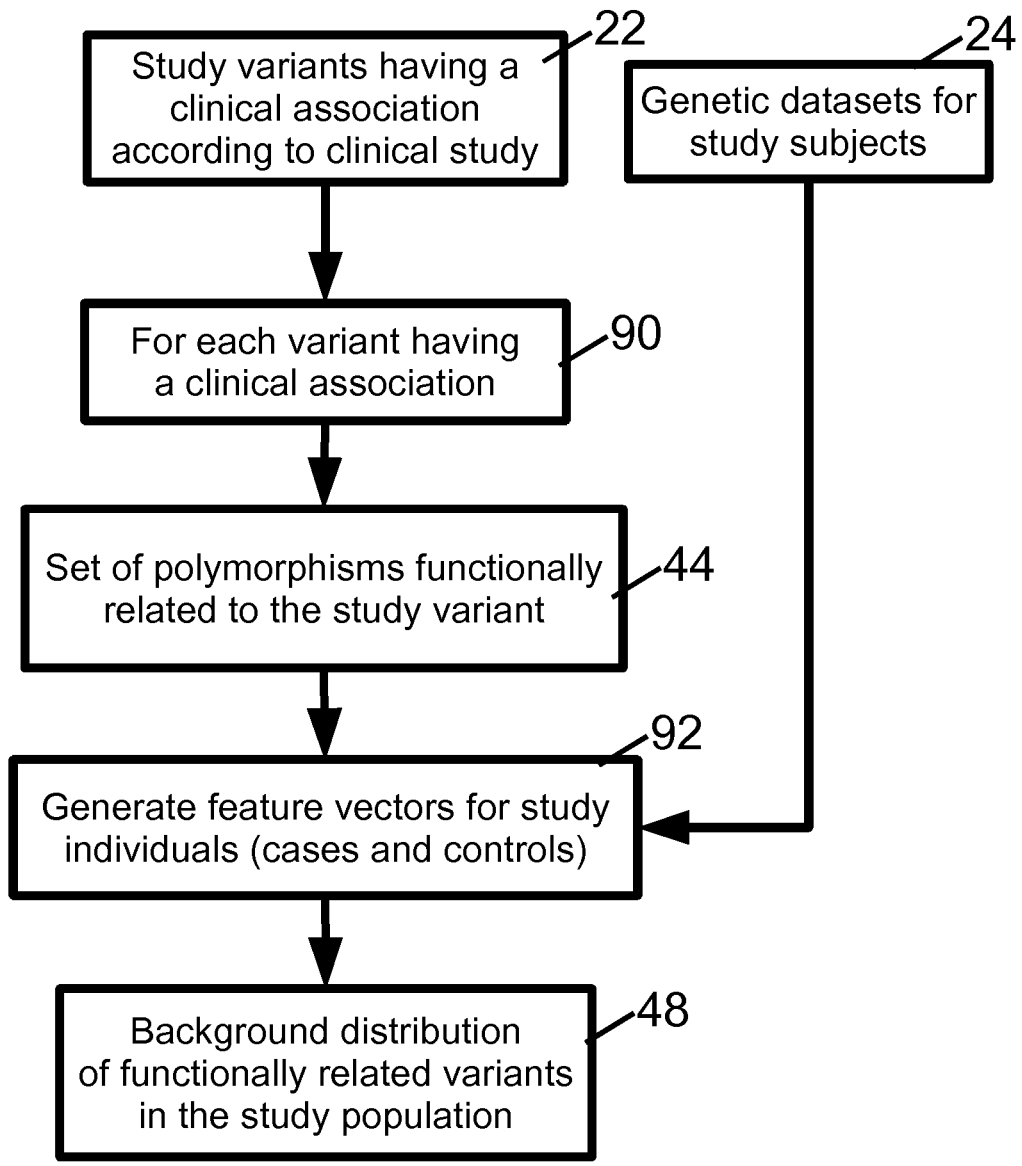

With returning reference to FIG. 1 and with further reference to FIG. 5, the operation 46 which generates the background distribution 48 of functionally related variants in the study population can employ various approaches. In the illustrative example of FIG. 5, for each study variant 90 the set of polymorphisms functionally related to that study variant 44 (which was generated by the operation 42, for example using one or more of the methods of FIGS. 2-4) is retrieved. In an operation 92, for each study subject the corresponding genetic dataset is retrieved from the set of genetic datasets 24 for the study subjects, and a feature vector is generated having vector elements storing variants observed in the subject for the set of polymorphisms 44.

Various types of formatting can be used for the values of the vector elements. In the case of SNPs, values may be stored as the actual nucleotides (or a numeric equivalent of the nucleotide, e.g. "0"=adenine, "1"=cytosine, "2"=guanine, "3"=thymine). Alternatively, the SNP value may be stored as a binary value, e.g. "0" if the SNP has its usual base value and "1" if the SNP has a base other than its usual base value. Other encodings can be used to store values for various other types of polymorphisms. The feature vectors for all the study subjects should have the same vector elements with the same formatting. For example, if vector element 7 stores the value of SNP x for one study subject, then the same vector element 7 should store the value of SNP x for all other study subjects.

In embodiments in which some subject genetic datasets may be incomplete such that not every polymorphism of the set of polymorphisms 44 can be determined for all subjects, a default "filler" value can be used to indicate that the value is unavailable, or alternatively the value can be filled with the most probable value (e.g., the value occurring most often in the population of the clinical study 22).

The output of the operation 92 is a set of feature vectors for the subjects of the clinical study 22. For example, if the clinical study 22 included N subjects, then the operation 92 outputs a corresponding N feature vectors. If all polymorphism of the set of polymorphisms 44 are encoded in the feature vectors with one vector element per polymorphism, then if the set of polymorphisms 44 includes R polymorphisms then the feature vectors have dimensionality R. The background distribution 48 is thus a set of N feature vectors of dimensionality R. In some embodiments this is stored as an N×R matrix (or, alternatively, as an R×N matrix).

Figure 6:
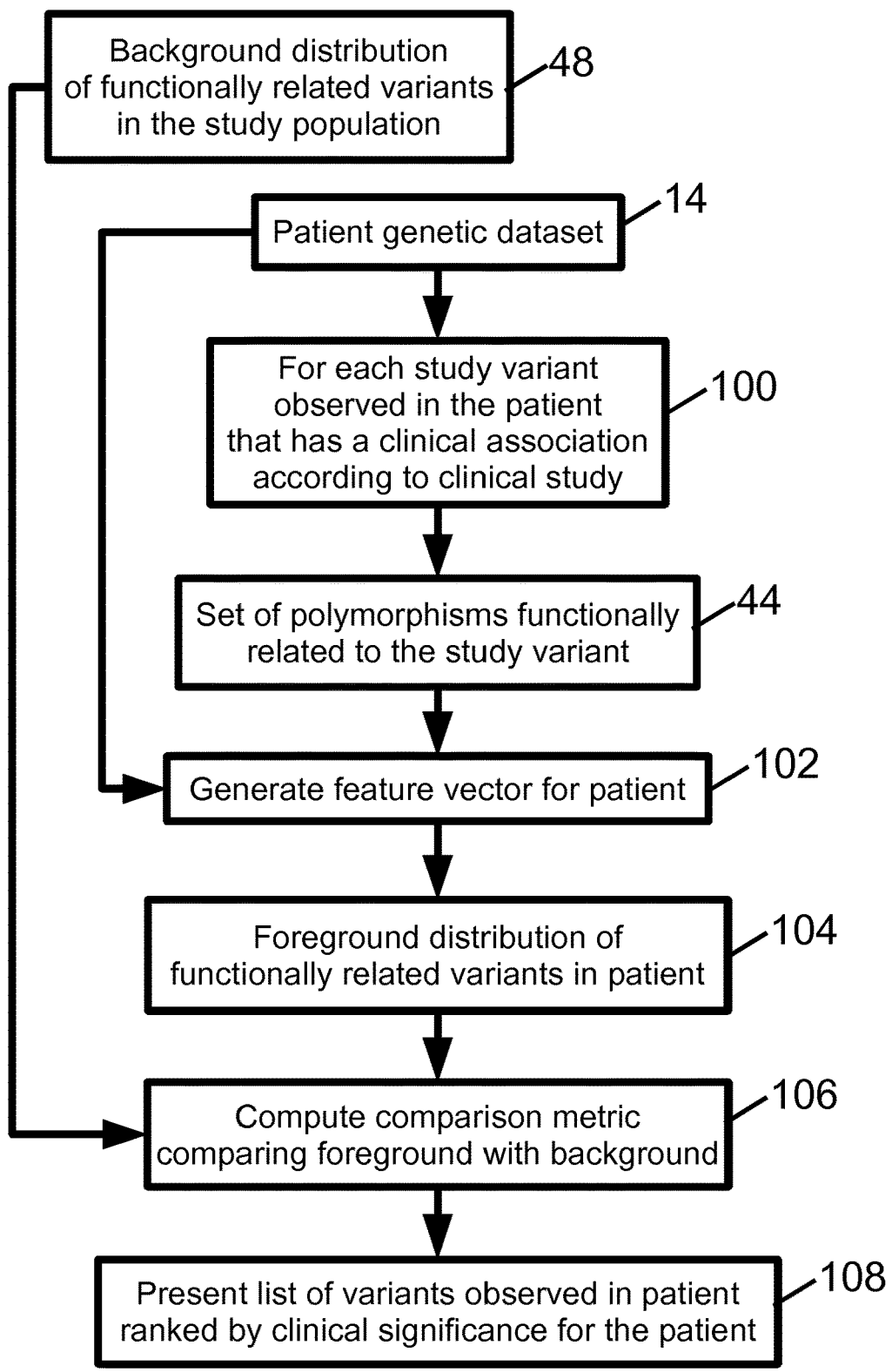

With returning reference to FIG. 1 and further reference to FIG. 6, an illustrative embodiment of the patient relevance assessment operations 34, 36 is described. The patient relevance assessment is performed for each variant 100 observed in the patient genetic dataset 14 that has a disease (or phenotype characteristic) association according to the clinical study 20. The set of polymorphisms 44 related to the study variant is retrieved, and in an operation 102 a patient feature vector for the patient is generated. The operation 102 is suitably performed in the same way as the operation 92 (see FIG. 5), except that the variants are obtained from the patient genetic dataset 14. The patient feature vector should have the same vector elements with the same formatting as the feature vectors generated in operation 92 for the study subjects. For example, if vector element 7 stores the value of SNP x in the feature vectors for the study subjects, then the same vector element 7 of the patient feature vector should store the value of SNP x for the patient. The resulting patient feature vector suitably serves as the foreground distribution 104 of functionally related variants in the patient.

In an operation 106, a comparison metric is computed which compares the foreground distribution 104 and the background distribution 48. In a straightforward approach, a distance (e.g., Euclidean distance) is computed between the patient feature vector and each study subject feature vector, and the distances are summed and optionally normalized by the number of subject feature vectors (N) to generate the comparison metric.

In another approach, a statistical significance metric is computed indicating the significance of the foreground distribution respective to the background distribution. For example, the statistical significance metric can be a Fisher exact test, a ks test, or a Wilconxon signed-rank test. A p-value computed by the statistical significance metric provides a suitable comparison metric.

Using either a distance metric or a statistical significance metric, a lower value of the distance or p-metric indicates closer similarity of the foreground distribution to the background distribution. A closer similarity corresponds to the patient being more similar to the study subjects, in a statistical sense, and with respect to parameters (the polymorphisms 44 related to the study variant) which are expected to be indicative of relevance of the study variant to the patient. Accordingly, a lower value of the distance or p-metric indicates higher relevance of the study variant to the patient, while a higher value of the distance or p-metric indicates less relevance of the study variant to the patient.

Other comparison metrics are contemplated. For example, in another approach the subject feature vectors are clustered to define a plurality of clusters, and an outlier metric is computed that measures distinctness of the patient feature vector from the clusters. In this case a higher outlier metric indicates greater distinctness from the clusters, corresponding to less relevance of the study variant to the patient.

In an operation 108, a list of genetic variants observed in the patient is presented (e.g., displayed on a display device, and/or printed on paper using a printer or other marking engine, or so forth) along with the clinical associations and an indication of relevance to the patient. This output can take various forms. In one approach, the variants are ranked according to relevance, with the most relevant variants at the top of the list. Such a list is optionally truncated, i.e. variants whose patient relevance falls below a certain threshold are not listed at all. For a distance or statistical significance comparison metric, relevance may suitably be quantified as an inverse of the distance or statistical significance metric such that a higher value of the distance or statistical significance metric indicates lower relevance of the study variant to the diagnostic subject. Various normalizations or other adjustments can be performed to provide a quantitative relevance measure that is readily comprehended by the physician or other reviewing medical personnel.

In another approach, only variants whose relevance exceeds a certain threshold are included in the list, but no quantitative patient relevance value is shown. In this case the patient relevance is implicitly included in the list insofar as inclusion of a variant on the list indicates that its patient relevance exceeds the threshold.

The diagnostic genetic analysis system of FIG. 1 can be variously implemented. In one approach, the diagnostic genetic analysis system is provided as a web-based service. A physician uploads the patient genetic dataset 14, and the website includes a server embodying the processing components 30, 40 and storing or having access to the relevant clinical study data 22, 24. The server performs the variant identification and relevance assessment operations disclosed herein, formulates a patient report based on the listing 108 or some similar output, and returns the patient report to the physician.

In another service paradigm, the service is provided via mail and includes the genetic data acquisition. In this case the physician sends the tissue sample 10 to the laboratory via mail, courier, or another convenient way, and the laboratory includes the processing components 30, 40, stores or has access to the relevant clinical study data 22, 24, and also includes the genetic data acquisition apparatus 12. All operations are performed at the service laboratory, and a patient report based on the listing 108 or some similar output is returned to the physician via mail, courier, or so forth.

In the illustrative embodiments, the single clinical study 20 is illustrated. It will be readily appreciated that this can be extended to diagnostic processing employing variants identified by two or more different clinical studies. In such cases, the background distribution for each variant is computed respective to the study population for the clinical study that published the variant-disease association.

As already noted, the processing components 30, 40 may optionally be integrated as a single processing component (e.g., a single computer, which may be a network server computer, a desktop computer, a notebook computer, a "cloud" computer comprising a network of computers, or so forth). Additionally, the disclosed variant identification and relevant assessment techniques can be embodied as a non-transitory storage medium storing instructions executable by a suitable electronic data processing device or devices 30, 40. The non-transitory storage medium may, for example, include: a hard disk drive or other magnetic storage medium; a random access memory (RAM), read-only memory (ROM), flash memory, or other electronic storage medium; an optical disk or other optical storage medium; various combinations thereof; or so forth.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A non-transitory storage medium storing instructions executable by an electronic data processing device to perform a method including:
identifying, from a plurality of polymorphisms in genetic data of a plurality of subjects of one or more clinical studies in a database of clinical studies, a plurality of sets of polymorphisms, each comprising a plurality of polymorphisms functionally related to a different study genetic variant that is associated by a clinical study with a phenotype characteristic, wherein genetic data for each subject comprises thousands or more genetic variants,
computing, by the electronic data processing device, for each of the plurality of sets of polymorphisms, a background distribution of variants within the set of polymorphisms, wherein computing each background distribution of variants in each set of polymorphisms comprises computing a subject feature vector for each subject of the clinical study having vector elements storing variants observed in the genetic data of that subject for the set of polymorphisms, and wherein the computed background distribution comprises a matrix of N subject feature vectors for R polymorphisms, where N is the plurality of subjects and R is the thousands or more genetic variants in the genetic data of each subject,
storing, by the electronic data processing device, the generated background distributions in a memory, each of the generated background distributions associated in memory with the computed subject feature vector for each subject of the clinical study,
receiving diagnostic subject genetic data comprising thousands or more genetic variants,
comparing, by the electronic data processing device, the diagnostic subject genetic data to the database of clinical studies,
identifying, from said comparison, a study genetic variant in the diagnostic subject genetic data,
identifying, from the plurality of sets of polymorphisms, the set of polymorphisms functionally related to the study genetic variant identified in the diagnostic subject genetic data,
computing, by the electronic data processing device, a foreground distribution of variants observed in the diagnostic subject genetic data for the identified set of polymorphisms,
retrieving, from the memory, the stored background distribution of the variants within the identified set of polymorphisms,
computing, by the electronic data processing device, a comparison metric comparing the foreground distribution and the retrieved background distribution,
quantifying, by the electronic data processing device, a relevance of the study variant to the diagnostic subject based on the comparison metric; and
providing to a medical personnel, via a user interface, a report comprising the study genetic variant identified in the diagnostic subject genetic data, and the quantified relevance of the study genetic variant to the diagnostic subject, and wherein
the computing of the foreground distribution of variants observed in the diagnostic subject genetic data for the set of polymorphisms includes computing a diagnostic subject feature vector having vector elements storing variants observed in the diagnostic subject genetic data for the set of polymorphisms.

2. The non-transitory storage medium of claim 1, wherein the identifying of a set of polymorphisms comprises:
identifying a genetic pathway with which the study genetic variant is associated; and
identifying polymorphisms associated with the identified genetic pathway.

3. The non-transitory storage medium of claim 2, wherein the identifying of the genetic pathway and the identifying of polymorphisms associated with the identified genetic pathway reference a genetic pathway database.

4. The non-transitory storage medium of claim 1 wherein the identifying of a set of polymorphisms comprises:
identifying polymorphisms having variants associated by one or more clinical studies with the phenotype characteristic with which the study variant is associated.

5. The non-transitory storage medium of claim 1 wherein the identifying of a set of polymorphisms comprises:
identifying a phenotype genetic signature that includes the study variant; and
identifying polymorphisms associated with the identified phenotype genetic signature.

6. The non-transitory storage medium of claim 1, wherein the computing of the comparison metric comparing the foreground distribution and the background distribution comprises:
clustering the subject feature vectors to define a plurality of clusters; and
computing an outlier metric measuring distinctness of the diagnostic subject feature vector from the clusters.

7. The non-transitory storage medium of claim 1, wherein the computing of the comparison metric comparing the foreground distribution and the background distribution comprises:
computing a statistical significance metric indicating the significance of the foreground distribution respective to the background distribution.

8. The non-transitory storage medium of claim 7, wherein the quantifying relevance of the study variant to the diagnostic subject based on the comparison metric comprises:
quantifying relevance as an inverse of the statistical significance metric such that a higher value of the statistical significance metric indicates lower relevance of the study variant to the diagnostic subject.

9. The non-transitory storage medium of claim 1, wherein the method further comprises:
repeating the identifying a study genetic variant, the identifying a set of polymorphisms, the computing a foreground distribution, the computing a background distribution, the computing a comparison metric, and the quantifying relevance of the study variant to identify and quantify relevance of a set of study genetic variants in the diagnostic subject genetic data, and displaying the study genetic variants ranked by relevance.

10. An apparatus comprising:
a non-transitory storage medium as set forth in claim 1; and
an electronic data processing device configured to execute the instructions stored on the non-transitory storage medium.

11. The non-transitory storage medium of claim 1, wherein the subject is a human.

12. A method comprising:
identifying, from a plurality of polymorphisms in genetic data of a plurality of subjects of one or more clinical studies in a database of clinical studies, a plurality of sets of polymorphisms, each comprising a plurality of polymorphisms functionally related to a different study genetic variant that is associated by a clinical study with a phenotype characteristic, wherein genetic data for each subject comprises thousands or more genetic variants;
computing for each of the plurality of sets of polymorphisms, a background distribution of variants within the set of polymorphisms, wherein computing each background distribution of variants in each set of polymorphisms comprises computing a subject feature vector for each subject of the clinical study having vector elements storing variants observed in the genetic data of that subject for the set of polymorphisms, wherein the computed background distribution comprises a matrix of N subject feature vectors for R polymorphisms, where N is the plurality of subjects and R is the thousands or more genetic variants in the genetic data of each subject;
storing the generated background distributions in a memory, each of the generated background distributions associated in memory with the subject feature vector for each subject of the clinical study;
receiving diagnostic subject genetic data comprising thousands or more genetic variants;
comparing the diagnostic subject genetic data to the database of clinical studies,
identifying, from said comparison, a study genetic variant observed in the diagnostic subject genetic data;
identifying, from the plurality of sets of polymorphisms, the set of polymorphisms functionally related to the study genetic variant identified in the diagnostic subject genetic data;
computing a foreground distribution of variants observed in the diagnostic subject genetic data for the identified set of polymorphisms;
retrieving, from the memory, the stored background distribution of the variants within the identified set of polymorphisms;
computing a comparison metric comparing the foreground distribution and the retrieved background distribution;
quantifying, by the electronic data processing device, a relevance of the study variant to the diagnostic based on the comparison metric; and
providing to a medical personnel, via a user interface, a report comprising the study genetic variant identified in the diagnostic subject genetic data, and the quantified relevance of the study genetic variant to the diagnostic subject wherein the identifying a set of polymorphisms, the computing a foreground distribution, the computing a background distribution, and the computing a comparison metric are performed by the electronic data processing device, and wherein:
the computing of the foreground distribution of variants observed in the diagnostic subject genetic data for the set of polymorphisms includes computing a diagnostic subject feature vector having vector elements storing variants observed in the diagnostic subject genetic data for the set of polymorphisms.

13. The method of claim 12, further comprising:
identifying the study genetic variant in the diagnostic subject genetic data;
wherein the diagnostic subject genetic data includes at least one of genetic sequencing data and microarray data.

14. The method of claim 12, wherein the identifying of a set of polymorphisms comprises:
identifying a genetic pathway with which the study genetic variant is associated; and
identifying polymorphisms associated with the identified genetic pathway.

15. The method of claim 12 wherein the identifying of a set of polymorphisms comprises:
identifying polymorphisms having variants associated by one or more clinical studies with the phenotype characteristic with which the study variant is associated.

16. The method of claim 12 wherein the identifying of a set of polymorphisms comprises:
identifying a phenotype genetic signature that includes the study variant; and
identifying polymorphisms associated with the identified phenotype genetic signature.

17. The method of claim 12, wherein the subject is a human.

18. A data storage and retrieval method for a computer memory using an electronic data processing device, comprising:
identifying, from a plurality of polymorphisms in genetic data of a plurality of subjects of one or more clinical studies in a database of clinical studies, a plurality of sets of polymorphisms, each comprising a plurality of polymorphisms functionally related to a different study genetic variant that is associated by a clinical study with a phenotype characteristic, wherein genetic data for each subject comprises thousands or more genetic variants;
computing, by the electronic data processing device, for each of the plurality of sets of polymorphisms, a background distribution of variants within the set of polymorphisms-, wherein computing each background distribution of variants in each set of polymorphisms comprises computing a subject feature vector for each subject of the clinical study having vector elements storing variants observed in the genetic data of that subject for the set of polymorphisms, and wherein the computed background distribution comprises a matrix of N subject feature vectors for R polymorphisms, where N is the plurality of subjects and R is the thousands or more genetic variants in the genetic data of each subject;
storing, by the electronic data processing device, the generated background distributions in the computer memory, each of the generated background distributions associated in memory with the computed subject feature vector for each subject of the clinical study;

receiving diagnostic subject genetic data comprising thousands or more genetic variants, comparing, by the electronic data processing device, the diagnostic subject genetic data to the database of clinical studies;

identifying, from said comparison, a study genetic variant in the diagnostic subject genetic data;

identifying, from the plurality of sets of polymorphisms, the set of polymorphisms functionally related to the study genetic variant identified in the diagnostic subject genetic data;

computing, by the electronic data processing device, a foreground distribution of variants observed in the diagnostic subject genetic data for the identified set of polymorphisms; and retrieving, from the computer memory, the stored background distribution of the variants within the identified set of polymorphisms, wherein the retrieved background distribution is utilized to: (i) compute a comparison metric comparing the foreground distribution and the retrieved background distribution; and (2) quantify a relevance of the study variant to the diagnostic subject based on the comparison metric.

19. The method of claim 18, wherein the subject is a human.

\* \* \* \* \*